US008409202B2

(12) United States Patent
Vasta

(10) Patent No.: US 8,409,202 B2
(45) Date of Patent: Apr. 2, 2013

(54) DRIVE SYSTEMS AND DEVICES INCORPORATING DRIVE SYSTEMS

(75) Inventor: Paul J. Vasta, McKinney, TX (US)

(73) Assignee: AMEI Technologies, Inc., Wilmington, DE (US)

(*) Notice: Subject to any disclaimer, the term of this patent is extended or adjusted under 35 U.S.C. 154(b) by 1009 days.

(21) Appl. No.: 11/408,617

(22) Filed: Apr. 21, 2006

(65) Prior Publication Data
US 2007/0012491 A1 Jan. 18, 2007

Related U.S. Application Data

(60) Provisional application No. 60/674,052, filed on Apr. 22, 2005.

(51) Int. Cl.
A61B 17/00 (2006.01)
(52) U.S. Cl. .......................................................... 606/59
(58) Field of Classification Search ............... 606/53–59; 74/351, 496, 400, 406, 424.83, 490.12, 415, 74/89.18, 416, 425, 490.09
See application file for complete search history.

(56) References Cited

U.S. PATENT DOCUMENTS

| 4,270,404 A | * | 6/1981 | Murakoshi et al. | ........ 74/490.09 |
| 4,449,301 A | * | 5/1984 | Backman | ...................... 33/32.6 |
| 4,782,842 A | | 11/1988 | Fietti, Jr. | |
| 5,056,523 A | * | 10/1991 | Hotchkiss et al. | ........... 600/427 |
| 5,160,337 A | * | 11/1992 | Cosman | ........................ 606/130 |
| 5,316,018 A | | 5/1994 | O'Brien | |
| 5,901,936 A | * | 5/1999 | Bieg | ............................. 248/370 |
| 5,941,877 A | | 8/1999 | Viegas et al. | |
| 6,044,722 A | * | 4/2000 | Fragnito | ........................ 74/351 |
| 6,277,118 B1 | * | 8/2001 | Grant et al. | ..................... 606/54 |
| 6,402,625 B2 | * | 6/2002 | Armstrong | ...................... 472/59 |
| 6,619,653 B2 | | 9/2003 | Dobrindt | |
| 6,632,092 B2 | * | 10/2003 | Moran | ............................ 434/55 |
| 6,678,562 B1 | * | 1/2004 | Tepper et al. | .................. 607/51 |
| 2004/0097985 A1 | | 5/2004 | Day et al. | |
| 2004/0101813 A1 | * | 5/2004 | Irion et al. | .................... 434/262 |
| 2004/0138659 A1 | * | 7/2004 | Austin et al. | .................... 606/54 |
| 2004/0204682 A1 | | 10/2004 | Smith | |

OTHER PUBLICATIONS

International Search Report for PCT/US06/15341 dated Apr. 21, 2006.

* cited by examiner

Primary Examiner — Eduardo C Robert
Assistant Examiner — Steven Cotroneo
(74) Attorney, Agent, or Firm — Baker & McKenzie LLP

(57) ABSTRACT

A fixation device may be used for supporting and/or stretching an injured body part. An exemplary fixation device uses a thumb wheel control element to provide controlled rotational micromovements of a joint. The control element and its associated drive system allow for movement along a particular axis, while the position remains fixed with relation to the other axis. In addition, the fixation device may incorporate a drive system that introduces a simultaneous longitudinal translation with rotation, in order to provide for a common point of origin of rotation between the fixation device and the affected body part supported by the fixation device.

19 Claims, 11 Drawing Sheets

DRIVE SYSTEMS AND DEVICES INCORPORATING DRIVE SYSTEMS

CROSS-REFERENCE TO RELATED APPLICATIONS

This application claims the benefit of U.S. Provisional Application No. 60/674,052, filed on Apr. 22, 2005. U.S. Provisional Application No. 60/674,052 is commonly assigned with the present application and is hereby incorporated by reference for all purposes.

FIELD OF THE INVENTION

The disclosed embodiments relate generally to medical device technology, and more specifically to orthopedic fixation devices for treating contracture and to the drive systems that allows precise control for positioning and locking such fixation devices.

BACKGROUND OF THE INVENTION

Oftentimes, injury to a joint or bone can result in contracture, an abnormal tightening or shortening of the muscles and/or ligaments that may act to prevent a normal range of motion for the affected body part. Contracture may also be a congenital condition restricting motion. Treatment regimens for contracture typically involve the use of a fixation device, such as a splint. The splint mechanism would usually be placed on the affected patient by medical personnel in such a way as to stretch and/or support the affected body part during the healing process, holding the affected body part in the proper position for treatment.

Treating contracture in joints can prove particularly problematic, since joints can undergo a wide range of motion. As a result, a fixation device which can accommodate a wide range of motions and which can allow medical professionals to precisely orient the affected body part may be needed in order to provide effective treatment options. A typical treatment regimen would require repeated visits to medical professionals so that the fixation device could be periodically adjusted, providing the necessary orientation to the affected body part and setting the proper amount of stretching and support for healing. So in order to provide effective treatment, a medical professional needs to be able to introduce precisely calibrated alterations to the position of the fixation device, and thereby the affected joint.

It is also important that the fixation device support the joint or bone in a way that corresponds to the natural range of motion for the joint/bone. Conventional fixation devices tend to introduce an unwanted compression to the joint socket or bone gap, since their point of origin for rotation is offset from that of the joint/bone. As the point of rotation is not the same for the affected body part and the fixation device, the body part is forced to absorb the difference, typically by deflecting to compress the gap between bones. This may introduce unwanted stress to the joint/bone that is the target of healing, slowing the healing process and possibly causing additional, unintentional injury.

So, there is a need for an improved fixation device that will allow medical professionals to make effective, calibrated adjustments to the positioning of the injured body part. Additionally, there is a need for a fixation device that provides for a common point of origin for rotation between the fixation device and the injured body part, preventing unintentional injury and speeding healing by ensuring that supported joints/bones are held in a natural alignment position.

SUMMARY

The present application discloses embodiments for a multi-directional drive system, typically used to control and fix splint-type elements for a fixation device. The drive system comprises a control element, such as a thumb wheel, and a drive element, such as a drive wheel, coupled to the control element such that the drive element can be driven to rotate about a first axis by rotation of the control element. A housing supports the control element and the drive element. A driven article, such as a substrate, is coupled with the drive element so as to be repositioned by rotation of the drive element.

The direction in which the driven article is repositioned depends on whether the drive system is in the first or second position. Often, the drive element has two locking positions, oriented so that they are angularly displaced from each other by ninety degrees, and by switching between the two positions of the drive element, the driven article may be positioned along one axis without affecting the position of the driven article along the other axis. This allows for precise orientation of the driven article using the drive element, controlled by the single control element.

When the drive system is turned to the first position, rotation of the drive element causes the driven article to move in a first direction, while when the drive system is turned to the second position, rotation of the drive element causes the driven article to move in a second direction. And while an exemplary embodiment might have the first and second positions angularly displaced from each other by 90°, the axes could be positioned through a wide range of angles. Indeed, alternative embodiments may allow for a range of motion not simply along two axes, but through a wide range of angles, by allowing the drive element to interact with the driven article as it pivots throughout its angular range of motion.

In a typical embodiment, such a drive system might be used to control and fix the movement of two elements of a joint. This would provide a simple and effective means for a medical professional to calibrate various splint-like elements of a fixation device so that a patient's joint may be held in proper alignment. Using a single simple thumb wheel control element, the doctor would be able to position and calibrate the elements of a fixation device with great precision in one direction at a time (while the other direction was held securely in place). This sort of controlled rotational micromovement would assist medical professionals much more in setting the proper alignment than the free rotation provided by common ball-joint systems, by ensuring that only intentional actuation would take place.

An external fixation device having a joint that incorporates such a drive system is also disclosed. The external fixation device comprises first and second portions connected by an adjustable joint. The adjustable joint comprises a drive system that includes a control element that can be used to rotate the first portion relative to the second portion. The first portion may include a clamp assembly for securing the first portion to a bone via one or more bone screws. The clamp assembly would be capable of being repositioned along a longitudinal axis that extends along the first portion such that the clamp assembly may be moved closer or further from the second portion.

In some embodiments, the position of the clamp assembly can be controlled by the control element so that the control element can simultaneously cause rotation of the first portion relative to the second portion and translation of the clamp assembly relative to the second portion. It may be especially useful to couple simultaneous translation in the longitudinal direction with rotation of the injured body part. Such an embodiment would allow for a single simple control element to provide precisely calibrated positioning of the fixation device (to stretch and support an injured body part in order to aid in healing), while also ensuring natural alignment of the bones by providing that the fixation device and the bones have a common point of origin of rotation.

The control element in such a fixation device may be moved between first and second positions. In the first position, the control element may be operable to rotate the first portion relative to the second portion in a generally horizontal plane. In the second position, the control element can be operable to rotate the first portion relative to the second portion in a generally vertical plane. Typically, an integrated locking mechanism also allows for rotation in only one direction at a time, and fixes the position of the drive element with respect to the driven article of the fixation device when switching between the two positions. This allows for precise calibration of the fixation device without the fear of introducing accidental movement. By using a drive system that incorporates the teachings of the present disclosure, rotation of the first portion in both the generally vertical and horizontal planes can be accomplished about a common point origin of rotation.

BRIEF DESCRIPTION OF THE DRAWINGS

Embodiments are illustrated by way of example in the accompanying figures, in which like reference numbers indicate similar parts, and in which.

DETAILED DESCRIPTION

Figure 1A:
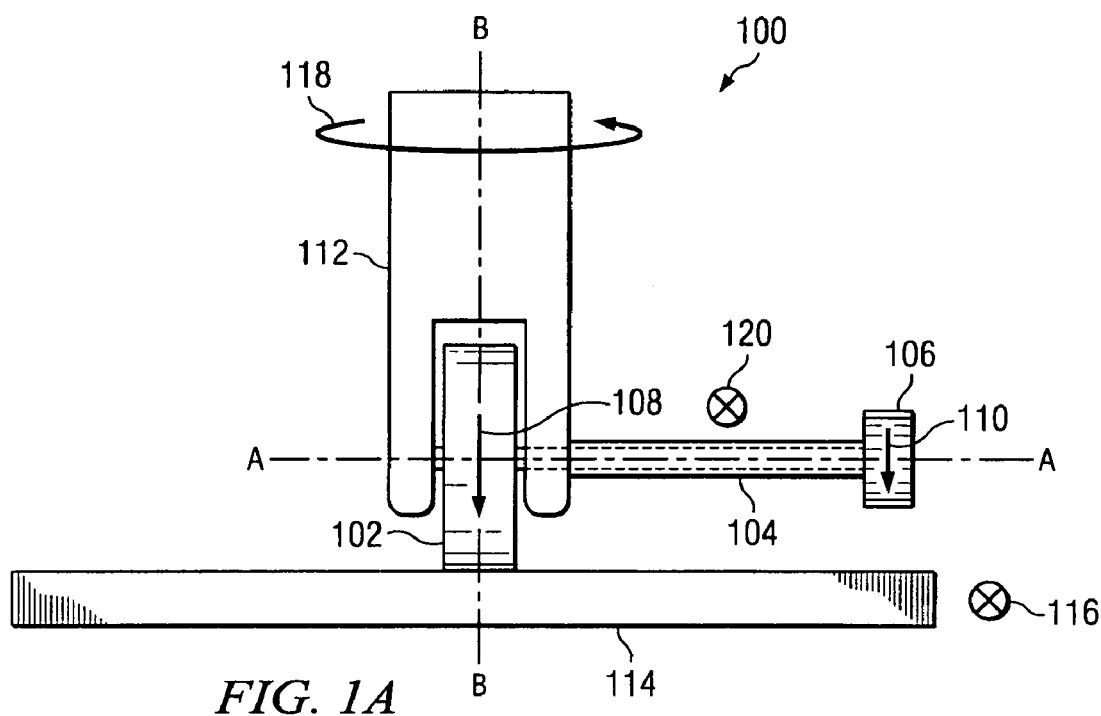
FIG. 1A shows an elevational view of an embodiment of a multi-directional drive system in a first position.

FIG. 1A shows an embodiment of a multi-directional drive system 100. The drive system 100 includes a drive wheel 102, which serves as a drive element, that can be driven to rotate by rotation of a thumb wheel 106, which serves as a control element. The thumb wheel 106 and the drive wheel 102 are connected by a drive shaft 104. The drive shaft 104 (shown in part with broken lines) extends along a longitudinal axis A-A and is fixed to the thumb wheel 106 such that it rotates about axis A-A as the thumb wheel 106 is rotated. The drive wheel 102 is fixed to the drive shaft 104 and rotates as the drive shaft 104 rotates. Thus, rotation of the drive wheel 102 can be controlled directly by rotation of the thumb wheel 106. For example, the drive wheel 102 can be rotated in the direction indicated by arrow 108 by rotating the thumb wheel in the direction indicated by arrow 110. Rotating the thumb wheel 106 in the opposite direction causes rotation of the drive wheel 102 in the opposite direction.

The drive wheel 102, drive shaft 104, and thumb wheel 106 are all supported by a support housing 112. The support housing 112 holds the drive wheel 102 in place such that, while the drive wheel 102 is free to rotate with rotation of the thumb wheel 106, the drive wheel 106 does not travel, but instead rotates in place.

The drive wheel 102 is frictionally coupled with a substrate 114 such that the substrate 114 is free to move under the influence of a drive force applied by rotation of the drive wheel 102. For example, rotation of the drive wheel 102 in the direction indicated by arrow 108 drives the substrate 114 in a direction that extends into the page as indicated at 116. Similarly, rotation of the drive wheel 102 opposite to the direction indicated by arrow 108 drives the substrate 114 in a direction that extends out of the page. Thus, the substrate 114 in FIG. 1A can be driven in two directions by rotation of the thumb wheel 106.

The support housing 112 is fixed in position so as to prevent translational motion of the drive wheel 102. The support housing 112 can, however, be rotated about the axis B-B. In one example, the support housing 112 can be rotated in the direction indicated by arrow 118 by pushing the thumb wheel 106 in a direction that extends into the page as indicated at 120.

Figure 1B:
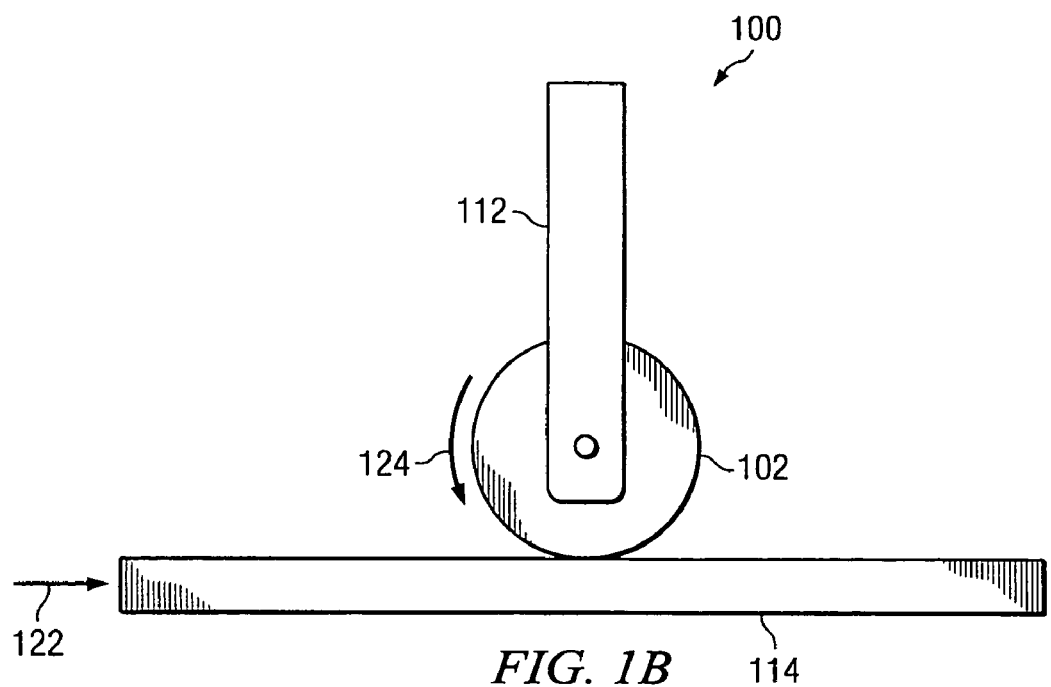
FIG. 1B shows an elevational view of the multi-directional drive system shown in FIG. 1A in a second position.

FIG. 1B shows the drive system 100 in a second position, where the drive system 100 is rotated 90° compared to the position of the drive system 100 as it is shown in FIG. 1A. With the drive system 100 positioned in this second position, the substrate 114 can be driven in a direction as indicated by arrow 122. With the substrate 114 frictionally coupled with the drive wheel 102, rotation of the drive wheel 102 in the direction indicated by arrow 124 exerts a force onto the upper surface of the substrate 114 causing the substrate 114 to be driven in the direction indicated by arrow 122. The drive wheel 102 can also be rotated in a direction opposite the direction indicated by arrow 124, which would cause the substrate 114 to be driven in a direction opposite the direction indicated by arrow 122.

The drive system 100 shown in FIGS. 1A and 1B provides a mechanically simple and efficient mechanism for driving an article in multiple non-parallel directions. The view shown in FIG. 1A shows the drive system 100 in a first position for driving, as an exemplary driven article, substrate 114 in directions that extend in and out of the page. The view shown in FIG. 1B shows the drive system 100 in a second position for driving the substrate 114 in directions that extend to the right and to the left across the page. Typically, the drive system 100 is capable of being rotated to be disposed in a first or second position according to a desired direction of translation of the substrate 114. It is contemplated, however, that the drive system 100 could be rotated to positions other than the two positions shown in FIGS. 1A and 1B, allowing for additional, alternative drive vectors.

In FIGS. 1A and 1B the substrate 114 is forced to move due to rotation of the drive wheel 102 provided that sufficient friction exists between the outer surface of the drive wheel 102 and the upper surface of the substrate 114. In the absence of sufficient friction, rotation of the drive wheel 102 may be ineffective for driving the substrate 114. For example, inadequate frictional coupling between the drive wheel 102 and the substrate 114 can result in intermittent or no movement of the substrate 114. In this regard, there are several measures that can be taken in order to ensure adequate friction between the drive wheel 102 and the substrate 114. The outer surface of the drive wheel 102 and/or the upper surface of the substrate 114 can be formed of a material, or coated with a material, that is conducive to providing an adequate friction joint. For example, surface asperities or other irregularities that increase the friction-joint surface area can be provided on the outer surface of the drive wheel 102 and/or the upper surface of the substrate 114.

Figure 2A:
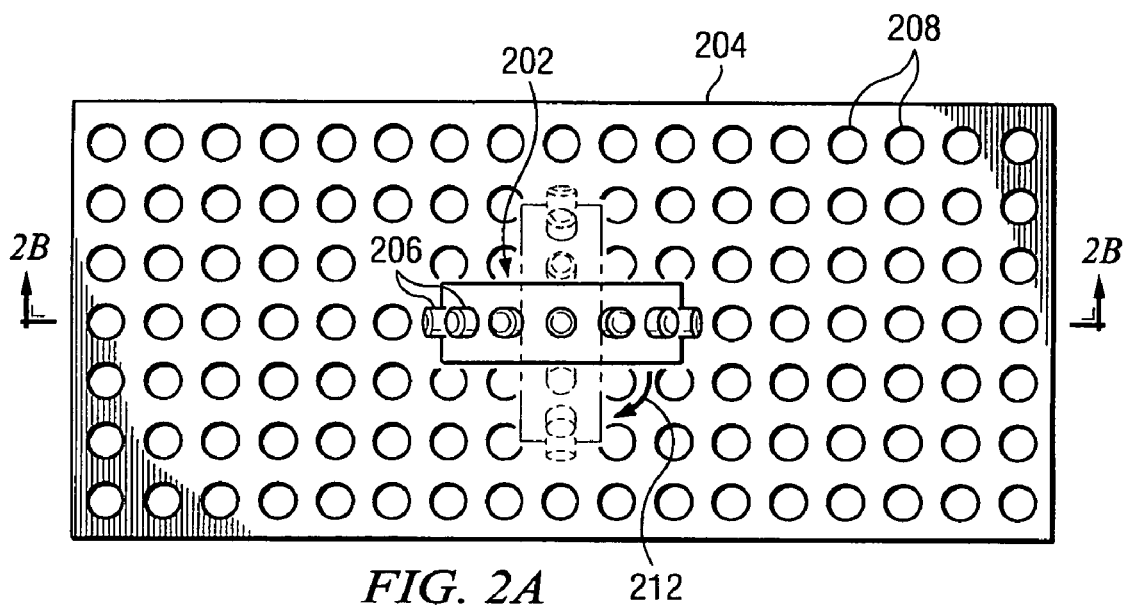
FIG. 2A shows a plan view of an alternative embodiment of a drive wheel.
Figure 2B:
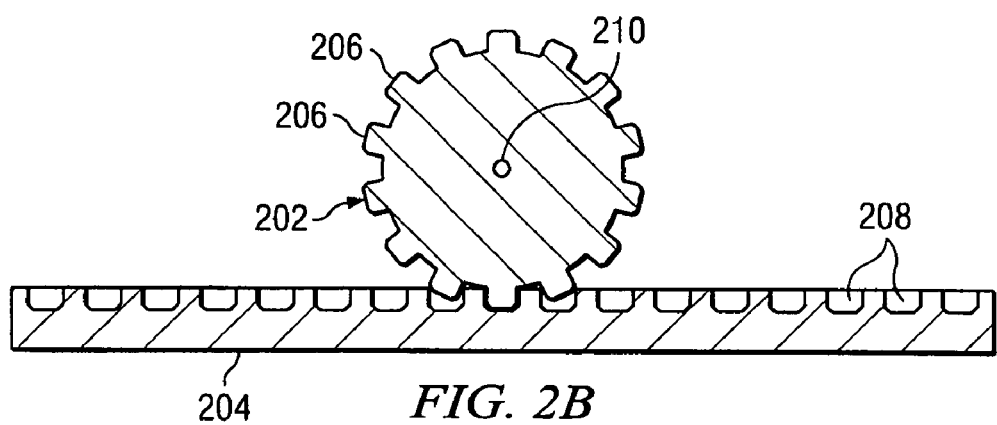
FIG. 2B shows a cross-sectional view taken along 2B-2B of FIG. 2A.

FIGS. 2A and 2B show an example of how the embodiment shown in FIGS. 1A and 1B can be modified in order to alter or replace the friction joint between the outer surface of the drive wheel 102 and the upper surface of the substrate 114. FIG. 2A shows a plan view of a cogged drive wheel 202, which serves as an alternative drive element, that can be used with a drive system such as the drive system 100 (in place of the drive wheel 102) shown in FIGS. 1A and 1B. FIG. 2B shows a cross-sectional view taken along section 2B-2B in FIG. 2A. Note that in the embodiment shown in FIGS. 2A and 2B, several components of the drive system 100 have been omitted for clarity.

The cogged drive wheel 202 includes a plurality of cogs 206, making it suitable for driving a substrate 204, which serves as a driven article, having a plurality of holes or recesses 208. As shown in FIG. 2A, the cogs 206 can mate with recesses 208 in order to provide a secure joint for driving the substrate 204 as the drive wheel 202 rotates. Note that characteristics of the cogs 206 and/or the recesses 208 can vary from what is shown in FIG. 2A. For example, the size, shape, and spacing of the cogs 206 and/or the recesses 208 can vary. Preferred arrangements of the cogs 206 and recesses 208 will allow for the cogs 206 to fit at least somewhat into successive recesses 208 as the drive wheel 202 rotates.

The cogged drive wheel 202 can be turned about its central axis or hub 210 (shown in FIG. 2B) by a drive system, for example drive system 100, in order to reposition the substrate 204. Referring to FIG. 2A, the cogged drive wheel 202 can also be turned, for example as indicated by arrow 212, in order to change the direction that the substrate 204 moves as the drive wheel 202 rotates about hub 210. In a first position (shown in solid lines), the drive wheel 202 can be rotated about hub 210 in order to reposition the substrate 204 in either of two directions that extend right and left across the page. The drive wheel 202 can be turned as indicated by arrow 212 from the first position to a second position (shown in broken lines). In the second position, the drive wheel 202 can be rotated about hub 210 in order to reposition the substrate 204 in either of two directions that extend up and down the page. The drive wheel 202 can be turned to be positioned in either of the two positions shown in FIG. 2A so that the substrate 204 can be repositioned in any of four directions extending up, down, right, and left across the page. In some embodiments, the drive wheel 202 can be moved away from the substrate 204 while it is being turned, particularly if the cogs 206 are arranged such that they would otherwise interfere with the ability of the wheel 202 to be turned.

Figure 3A:
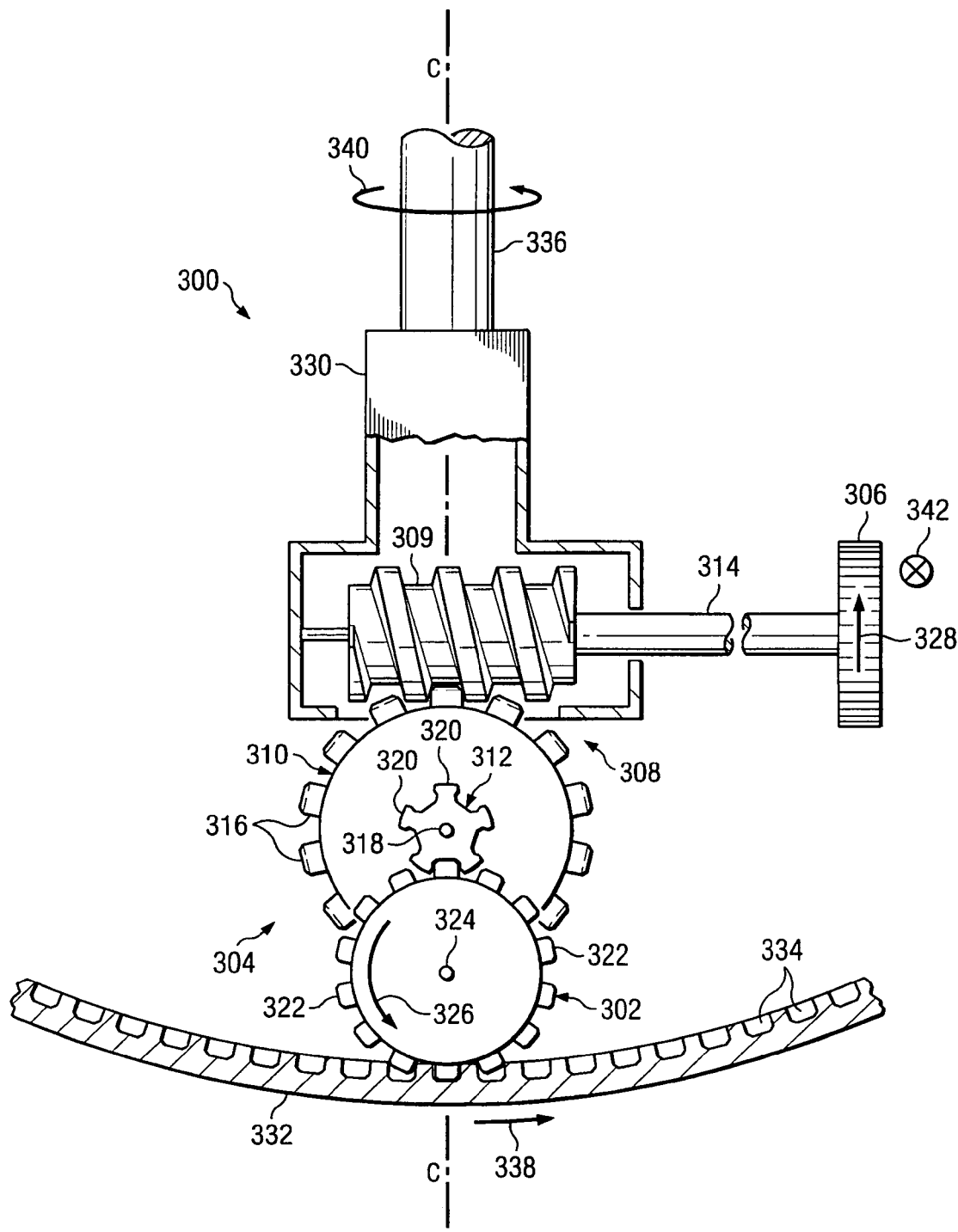
FIG. 3A shows an elevational view of an alternative embodiment of a multi-directional drive system in a first position.
Figure 3B:
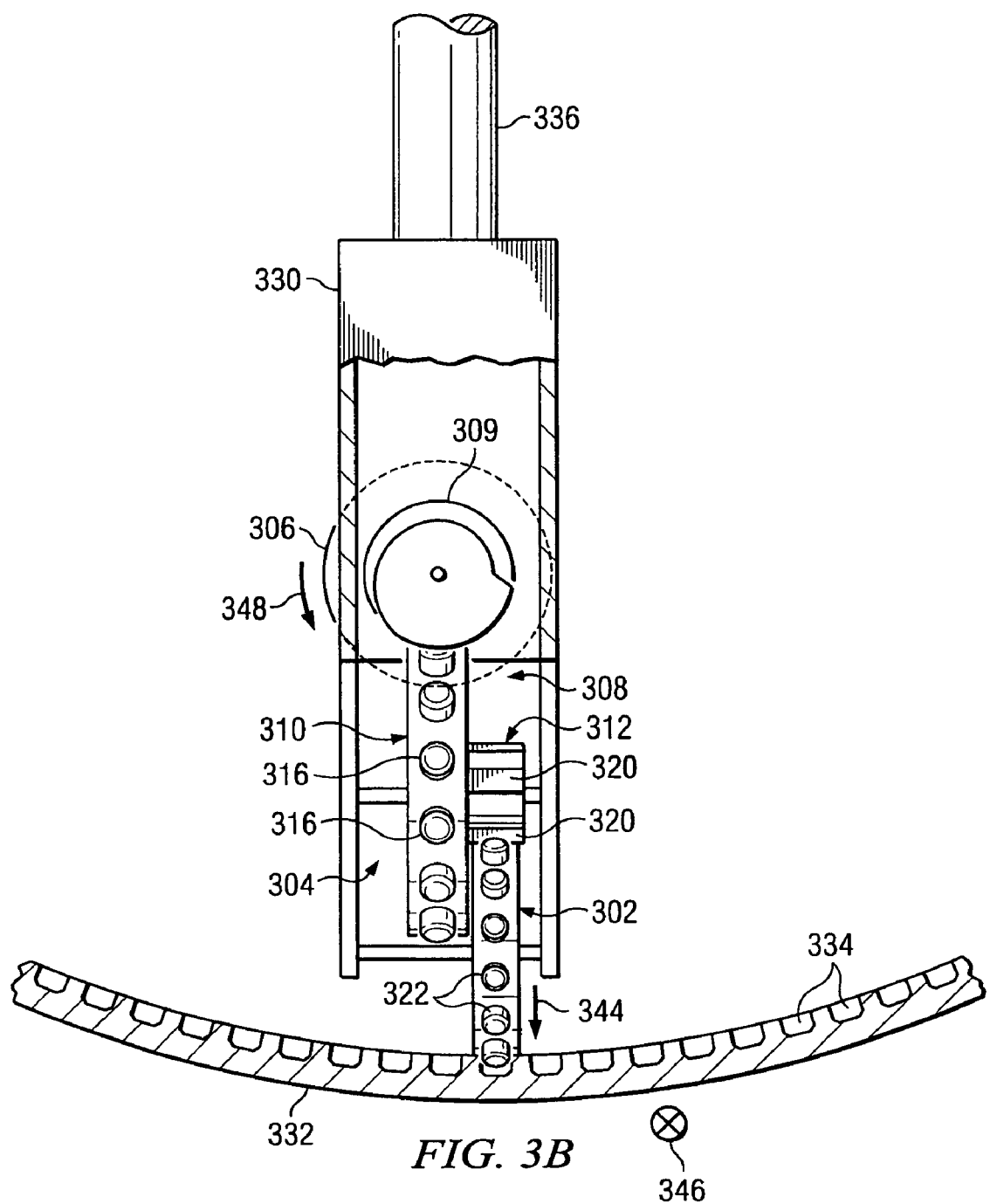
FIG. 3B shows an elevational view of the multi-directional drive system shown in FIG. 3A in a second position.

FIGS. 3A and 3B show a drive system 300 which can serve as an alternative embodiment to drive system 100. The drive system 300 includes a cogged drive wheel 302, which serves as a drive element, that can be driven to rotate by rotation of a thumb wheel 306, which serves as a control element. The thumb wheel 306 and the drive wheel 302 are connected by a gear system 304. In one embodiment, the gear system 304 includes a worm gear 308, which includes a worm 309 and a worm wheel 310. The gear system 304 also includes a gear 312 fixed to the worm wheel 310 for driving the drive wheel 302.

The thumb wheel 306 is connected to the worm 309 of the worm gear 308 via a shaft 314. The shaft 314 translates rotation of the thumb wheel 306 to the worm 309 so that the worm 309 rotates according to rotation of the thumb wheel 306. The worm 309 meshes with teeth 316 of the worm wheel 310. As the worm 309 is rotated, it exerts a force against successive teeth 316 of the worm wheel 310 resulting in rotation of the worm wheel 310 about its hub 318. The gear 312 is fixed to the worm wheel 310 such that the gear 312 rotates about the hub 318 as the worm wheel 310 rotates about the hub 318. The gear 312 has teeth 320 that mesh with cogs 322 of the drive wheel 302. As the gear 312 rotates, successive teeth 320 exert a force against successive cogs 322 of the drive wheel 302 causing the drive wheel 302 to rotate about hub 324. Thus, rotation of the drive wheel 302 can be controlled by rotation of the thumb wheel 306. For example, the drive wheel 302 can be rotated in the direction indicated by arrow 326 by rotating the thumb wheel 306 in the direction indicated by arrow 328. Rotating the thumb wheel 306 in the opposite direction causes rotation of the drive wheel 302 in the opposite direction.

The drive wheel 302, gear system 304, shaft 314, and thumb wheel 306 are all supported by the drive housing 330. The support housing 330 holds the drive wheel 302 in place such that, while the drive wheel 302 is free to rotate about hub 324 with rotation of the thumb wheel 306, the drive wheel 306 does not travel, but instead rotates in place.

The drive wheel 302 is coupled with a substrate 332, which serves as a driven article, via the cogs 322 of the drive wheel 302 that can mesh with recesses 334 formed in a surface of the substrate 332. An optional resilient member 336 can be provided for biasing the drive wheel 302 towards the substrate 332. The resilient member 336 can be, for example, a spring. The resilient member 336 allows for the drive wheel 302 to be withdrawn from the surface of the substrate 332 as necessary, for example in order to turn the drive wheel 302.

The substrate 332 is disposed such that it is free to move under the influence of a drive force applied by rotation of the drive wheel 302. Rotation of the drive wheel 302 in the direction indicated by arrow 326 drives the substrate 332 in a direction indicated by arrow 338. Similarly, rotation of the drive wheel 302 opposite to the direction indicated by arrow 326 drives the substrate 332 in a direction opposite the direction indicated by arrow 338. Thus, the substrate 332 can be driven in two directions by rotation of the thumb wheel 306.

The support housing 330 is fixed in position so as to prevent translational motion of the drive wheel 302. The support housing 330 can, however, be rotated about the axis C-C. The support housing 330 can be rotated in the direction indicated by arrow 340 by pushing the thumb wheel 306 in a direction that extends into the page as indicated at 342.

FIG. 3B shows the drive system 300 in a second position, where the drive system 300 is rotated 90° compared to the position of the drive system 300 as it is shown in FIG. 3A. With the drive system 300 positioned in this second position, the substrate 332 can be driven in a direction that extends in and out of the page. With one or more recesses 334 of the substrate 332 meshed with a cog or cogs 322 of the drive wheel 302, rotation of the drive wheel 302 in the direction indicated by arrow 344 causes the substrate 332 to be driven in a direction that extends into the page as indicated at 346. Note that rotation of the drive wheel 302 in the direction indicated by arrow 344 can be generated by rotating the thumb wheel 306 in the direction indicated by arrow 348. The drive wheel 302 can also be rotated in a direction opposite the direction indicated by arrow 344, which would cause the substrate 332 to be driven in a direction that extends out of the page and opposite the direction indicated at 346.

Figure 3C:
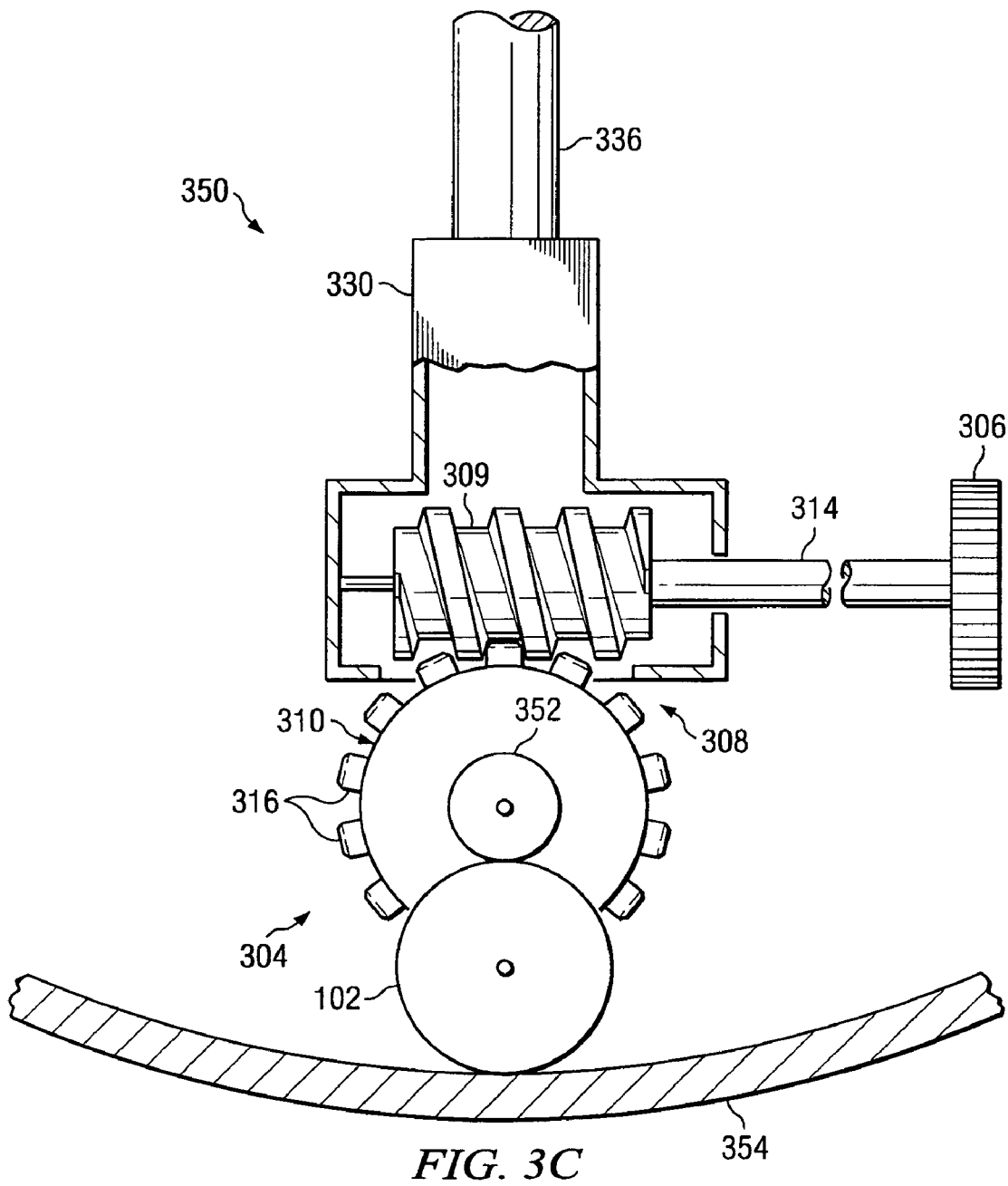
FIG. 3C shows an elevational view of the multi-directional drive system shown in FIG. 3A with an alternative drive wheel.
Figure 3D:
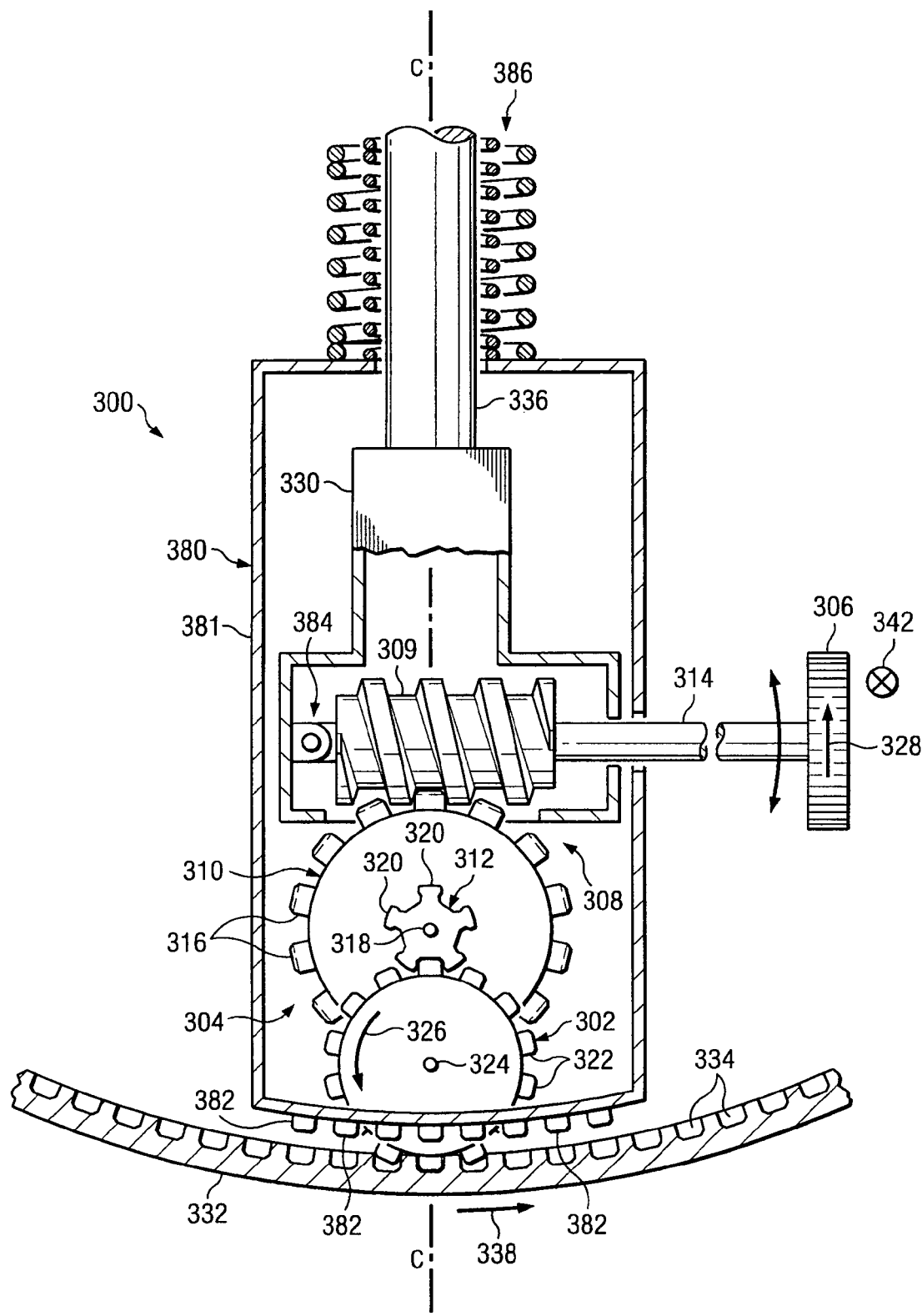
FIG. 3D shows a cut-away elevation view of a multi-directional drive system with a cylindrical sheath locking mechanism.

FIG. 3D illustrates another optional element that can be used in conjunction with the basic mechanisms shown in FIGS. 3A and 3B. Specifically, FIG. 3D illustrates an embodiment with an incorporated locking mechanism 380 designed to engage the substrate 332 to prevent unwanted movement. In general, incorporating a locking mechanism 380 within the drive system 300 provides for controlled rotational micro-movements that occur only through intentional actuation of the drive system 300; driven elements would not be allowed to rotate freely with respect to one another, but would be locked so that they may only rotate in a single direction at once based upon movements of the control element 306. In other words, whenever the drive system 300 is not engaged with the substrate 332 of the driven article (as for example, when the drive system 300 is pivoting between positions), the locking mechanism 380 would hold the driven article in place relative to the drive system 300.

In the disclosed embodiment, the locking mechanism 380 comprises a cylindrical sheath 381 disposed about the drive system 300. The cylinder 381 has teeth 382 along its bottom edge, which mesh with the recesses 334 of the substrate 332 to prevent motion of the substrate 332 whenever the locking mechanism 380 is engaged. A spring mechanism 386 may provide the downward force of engagement for the disclosed locking mechanism 380.

In this embodiment, the spring 386 holds the cylinder 381 in place against the substrate 332 whenever the drive system 300 is pivoting between positions. The shaft 314 may operate as both the driving rod for the gears and a lever for engaging/disengaging the locking mechanism 380. By way of example, the shaft 314 may include a hinge 384, that allows it to pivot upward and downward in relation to the substrate 332 in order to effect engagement. The shaft 314 may pivot to force the locking mechanism 380 away from the substrate 332, while bringing the drive system 300 into engagement with the substrate 332. Likewise, the shaft 314 can be used to bring the locking mechanism 380 into engagement with the substrate 332 while forcing the drive system 300 away from the substrate 332 (as for example, when preparing to pivot the drive system 300 between its two positions). The engagement of both the locking mechanism 380 and the drive system 300 can be assisted by a spring mechanism 386.

Figure 3E:
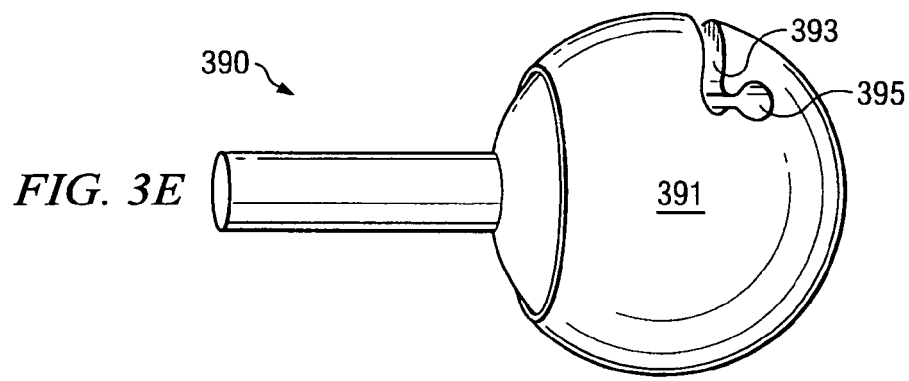
FIG. 3E shows an elevation view of an adjustable joint having a keyholed slot for use with a locking multi-directional drive system, such as that shown in FIG. 3D.

And when such a drive system 300 is used within a joint element 390 (as described below), a slot 393 within the joint housing 391 can be shaped to aid in both the engagement and disengagement of the locking mechanism 380. Such a slot 393 for a joint housing 391 is illustrated in FIG. 3E, which shows a slot 393 with a keyhole offset 395 that may be used in conjunction with the shaft 314 to guide the locking mechanism 380 between positions. By way of example, if the shaft 314 of the drive system 300 is moved into the keyhole 395, it acts as a lever to disengage the locking mechanism 380 from the substrate 332 and to engage the drive system 300. To do so effectively, the shaft 314 may have a notch that allows it to enter into the keyhole 395 when depressed towards the center of the joint housing 391. Alternatively, whenever the shaft 314 is located anywhere in the slot 393 (rather than the keyhole 395, the locking mechanism 380 would be engaged and the drive system 300 would be capable of being rotated to either 90° position.

Such a locking mechanism 380 could also be used with a frictional coupling drive system, such as that of FIGS. 1A and 1B, and would operate similarly except for the use of frictional engagement of the cylinder with the substrate 332 rather than employing teeth 382 to engage recesses 334 in the substrate 332. Persons skilled in the art field will appreciate that other types of locking mechanisms 380 could also be used to lock the substrate 332 in place whenever the position of the drive system 300 is altered. The locking mechanism 380 of FIG. 3D is simply one example; any equivalent locking mechanisms are included within the scope of this disclosure.

Thus, a difference between the drive system 100 shown in FIGS. 1A and 1B and the drive system 300 shown in FIGS. 3A and 3B is that the drive system 300 includes a gear system (gear system 304) between the thumb wheel 306 and the drive wheel 302. While the drive system 100 is shown as a friction-drive system and the drive system 300 is shown as a cogged-wheel drive system, these aspects of the two embodiments can be considered interchangeable. That is, the drive system 100 can be readily modified to include a cogs on the drive wheel 102 and the drive system 300 can be readily modified to have drive wheel 302 free of the cogs 322. Also, it will be noted that the cross-sectional shape of the driven article can vary. The drive system 100 and the drive system 300 can be used with a substrate or driven article having a substantially planar cross-section, for example as shown in FIGS. 1A and 1B, or a substantially non-planar cross-section, for example as shown in FIGS. 3A and 3B, or other planar or non-planar shapes.

The view shown in FIG. 3A shows the drive system 300 in a first position for driving, as an exemplary driven article, substrate 332 in directions that extend to the right and to the left across the page. The view shown in FIG. 3B shows the drive system 300 in a second position for driving the substrate 332 in directions that extend in and out of the page. The drive system 300 can be rotated to be disposed in the first or second position according to a desired direction of translation of the substrate 332. It is contemplated that the drive system 300 could be rotated to positions other that the two positions shown in FIGS. 3A and 3B, allowing for additional, alternative drive vectors.

FIG. 3C shows a drive system 350, which is similar to the drive system 300 except that a friction-drive wheel 102 (shown in FIGS. 1A and 1B) is used in place of the cogged drive wheel 302. Also, a wheel 352 is used in place of the gear 312 for rotating the drive wheel 102. The wheel 352 is fixed to worm wheel 310 and frictionally coupled with the drive wheel 102. Thus, rotation of the thumb wheel 306 causes rotation of the drive wheel 102 via the worm gear 308 and the wheel 352. The drive wheel 102 is frictionally coupled with the surface of the substrate 354, which serves as a driven article. The outer surface of the drive wheel 102 and/or the upper surface of the substrate 354 can be formed of a material, or coated with a material, that is conducive to providing an adequate friction joint.

Figure 4A:
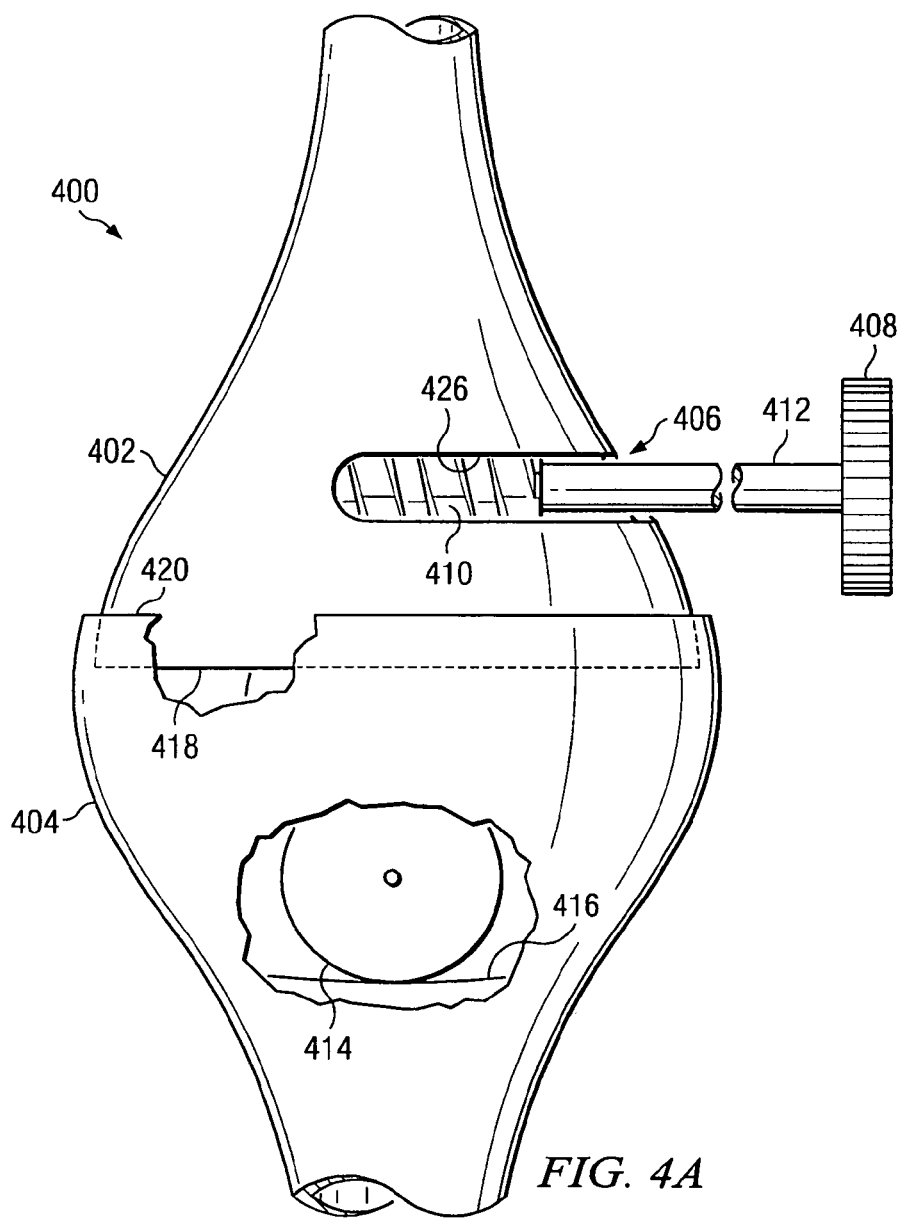
FIG. 4A shows an elevational view of an embodiment of an adjustable joint having a drive system positioned in a first position.
Figure 4B:
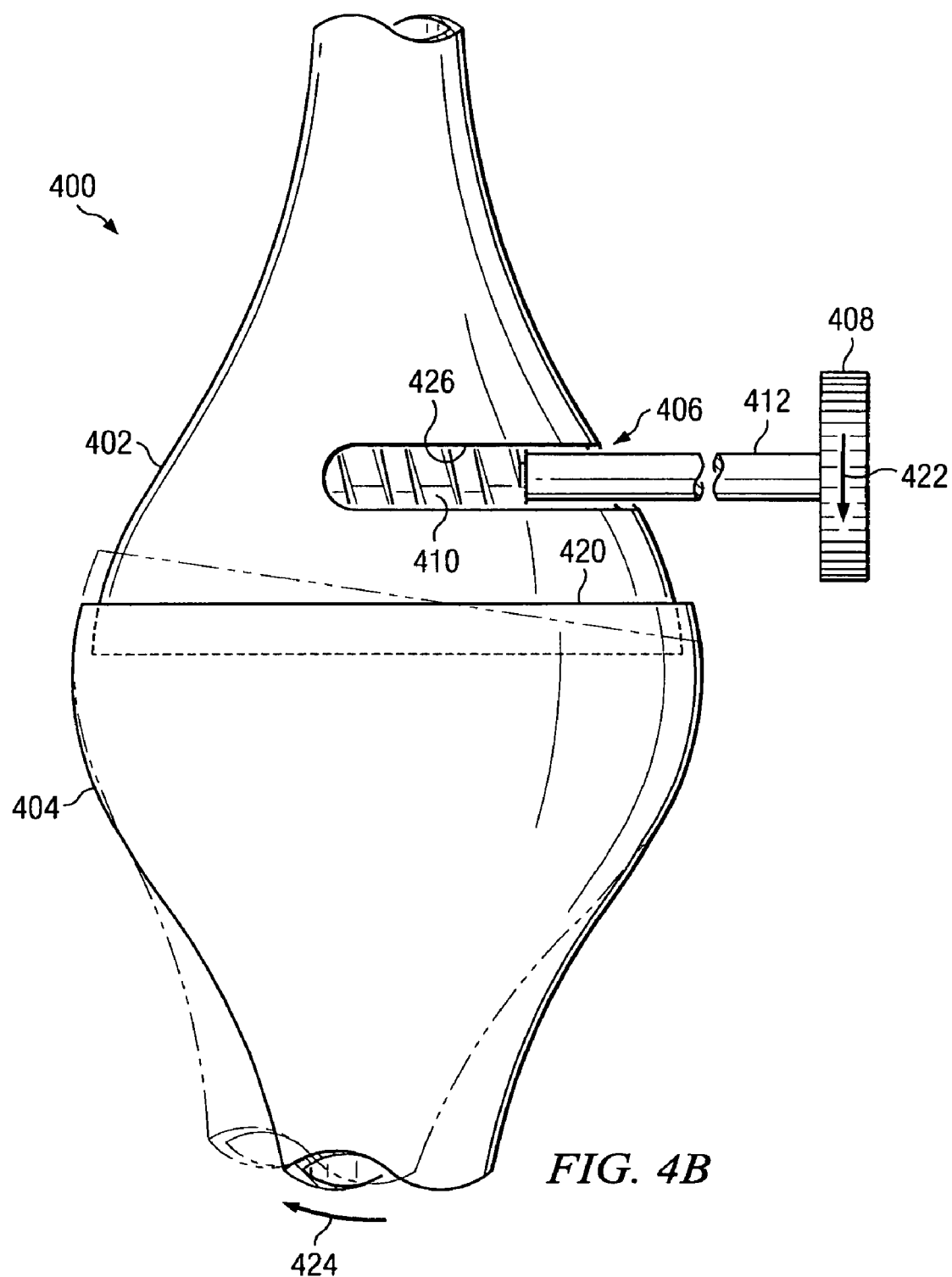
FIG. 4B shows an elevational view of the adjustable joint shown in FIG. 4A, illustrating an example of the rotational motion of the joint.
Figure 4C:
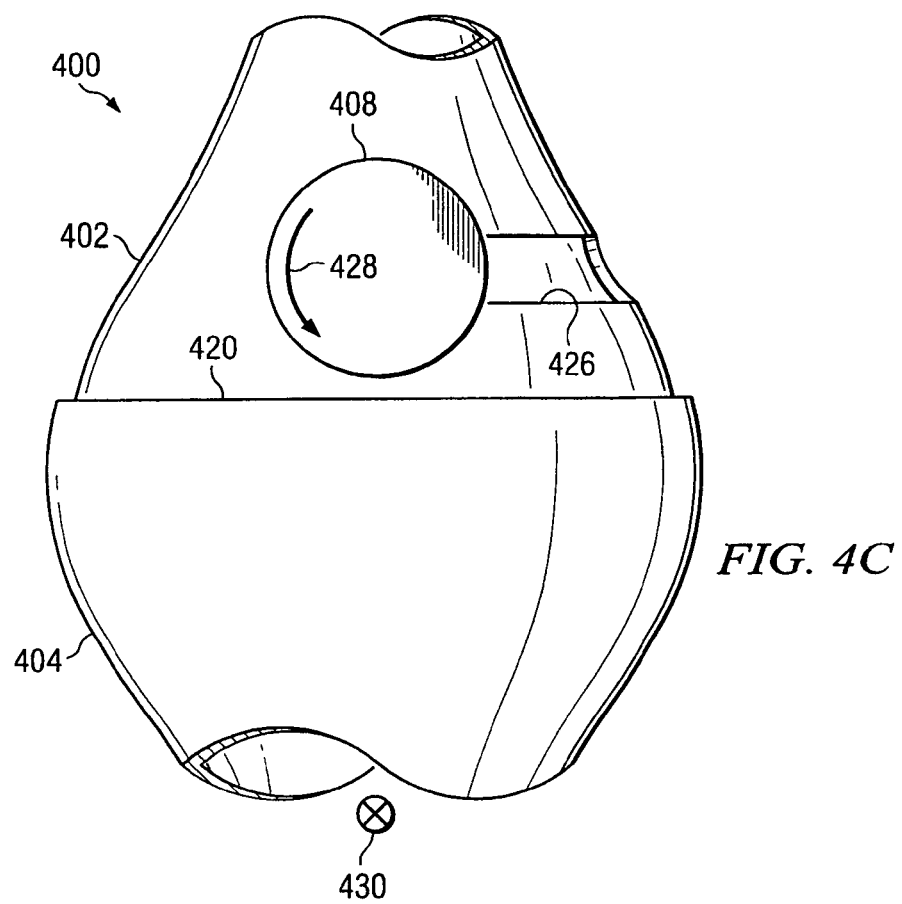
FIG. 4C shows an elevational view of the adjustable joint shown in FIG. 4A having the drive system positioned in a second position.

Turning next to FIGS. 4A-4C, an adjustable joint 400 will be described that incorporates a drive system such as any of the embodiments described herein. Such an adjustable joint 400 would be useful, by way of example, in positioning the elements of a fixation device, allowing for precise, calibrated movements in order to provide proper alignment of the fixation device (and thereby the injured body part) for healing. One feature of the adjustable joint 400 is that it allows for rotation of one element relative to another element in two different planes about a common origin of rotation. The joint 400 comprises a housing 402 and a socket member 404. The view shown in FIG. 4A includes a partially cut-away view of socket member 404 for purposes of clarity. The housing 402 at least partially houses a drive system 406. Any of the drive systems 100, 300, or 350, or equivalents thereof can be used as the drive system 406. In the illustrated embodiment, the drive system 406 includes a thumb wheel 408, which serves as a control element, and a worm 410 connected by a shaft 412. The drive system 406 also includes a drive wheel 414, which serves as a drive element. The drive wheel 414 is rotated by rotation of the thumb wheel 408. The drive wheel 414 is frictionally coupled with a contact surface 416 of the socket member 404 such that rotation of the thumb wheel 408 causes the surface 416 to move relative to the drive wheel 414.

As oriented in the view shown in FIG. 4A, the housing 402 has a lower edge 418 that fits inside the socket member 404 below an upper edge 420 of the socket member 404. The outer diameter of the lower edge 418 is larger than the inner diameter of the upper edge 420 so that the socket member 404 and housing 402 can be held together. Similarly, alternative configurations could be employed to form the adjustable joint 400. One alternative, by way of example, would be to essentially reverse the configuration set forth above, with the socket formed having an upper edge that would fit inside the housing above the lower edge of the housing and the diameter of the upper edge being larger than the inner diameter of the lower edge.

Referring additionally now to FIG. 4B, the socket member 404 can be rotated relative to the housing 402. The angular displacement of the socket member 404 is controlled by rotating the thumb wheel 408. For example, as shown in FIG. 4B, by rotating the thumb wheel 408 in the direction indicated by arrow 422 the socket member 404 can be rotated from the position shown in solid lines to an angularly displaced position shown in broken lines in the direction indicated by arrow 424. The socket member 404 can also be rotated, for example from the position shown in broken lines to the position shown in solid lines, in a direction opposite the direction indicated by arrow 424 by rotating the thumb wheel 408 in a direction opposite the direction indicated by arrow 422.

Thus, in the arrangement shown in FIGS. 4A and 4B, the socket member 404 can be angularly displaced in a first plane in directions that extend left and right across the page by rotation of the thumb wheel 408. The drive system 406 can be turned approximately 90° from the position shown in FIG. 4A to the position shown in FIG. 4C. A shaft slot 426 provides clearance for the shaft 412 to move between the position shown in FIG. 4A to the position shown in FIG. 4C. With the drive system 406 in the position shown in FIG. 4C, the socket member 404 can be angularly displaced in a second plane in directions that extend in and out of the page by rotation of the thumb wheel 408. For example, by rotating the thumb wheel 408 in the direction indicated by arrow 428 the socket member 404 can be rotated in the direction indicated at 430 to an angularly displaced position. The socket member 404 can also be rotated in a direction opposite the direction indicated at 430 by rotating the thumb wheel 408 in a direction opposite the direction indicated by arrow 428.

Thus, as will be appreciated by the views provided in FIGS. 4B and 4C and the description provided above, an adjustable joint can be realized that allows for rotation of one element relative to another element in two different planes about a common origin of rotation. For example, in the configuration shown in FIG. 4B the socket member 404 can be rotated (relative to the housing 402) in a first plane, while in the configuration shown in FIG. 4C the socket member 404 can be rotated (relative to the housing 402) in a second plane that is generally orthogonal to the first plane. In both of FIGS. 4B and 4C, the socket member 404 rotates about a common origin of rotation.

Figure 4D:
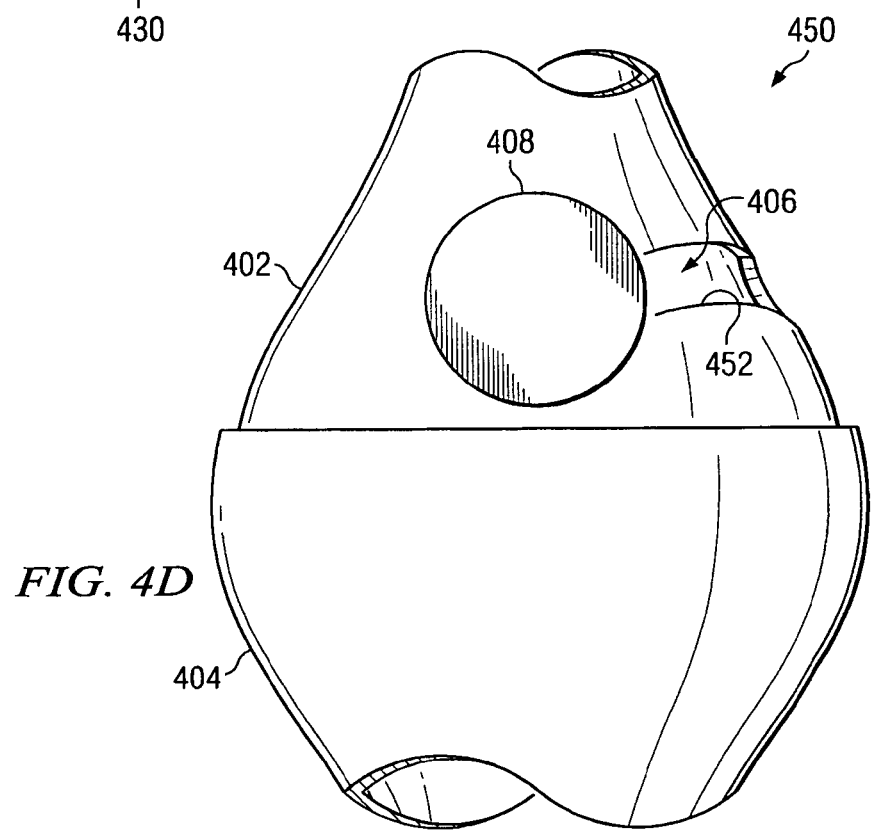
FIG. 4D shows an elevational view of the adjustable joint shown in FIG. 4A with an alternative shaft slot configuration.

FIG. 4D shows an adjustable joint 450 that is similar to the adjustable joint 400 except that the shaft slot 426 is replaced with a curved shaft slot 452. The curved shaft slot 452 forces the drive system 406 to move away from the socket member 404 as the drive system 406 is turned between the two positions shown in FIGS. 4A and 4C. As the drive system 406 is being turned, the shaft 412 rides the contour of the curved slot 426. The remaining components of the drive system 406 remain fixed relative to the position of the shaft 412, so as the shaft 412 is moved away from the socket member 404 and back by the contour of the curved slot 452 the balance of the drive system 406 is moved as well.

Moving the drive system 406 away from the socket member 404 can ease the effort required for turning the drive system 406 by reducing the friction between the drive wheel 414 and the surface 416 (shown in FIG. 4A) that would otherwise oppose the turning of the drive system 406. Although not shown, in some embodiments, a cylindrical-like mechanism may be disposed inside the housing 402 and around the drive system 406 for temporarily holding the socket member 404 in place as the drive system 406 is being turned or as a locking mechanism when the desired displacement of socket member 404 is obtained. In practice, the shaft 412 would force the cylindrical-like mechanism, or locking cylinder, against the socket member 404 to hold the socket member in place. By way of example, a locking mechanism such as that shown in FIGS. 3D and 3E could be employed.

The adjustable joints 400 and 450 of the disclosed embodiments can be used in any system where a rotatable joint is desired, particularly if a joint is desired that can be controlled to rotate in multiple dimensions about a single axis of rotation. Such a joint allows for simple yet precise control of the movements of the joint elements (typically a socket member and a joint housing), and may be useful in a wide range of medical devices. By way of a specific example, such a joint may prove useful within a fixation device, of the type described below, by allowing for precise orientation of the injured body part for healing.

Figure 5:
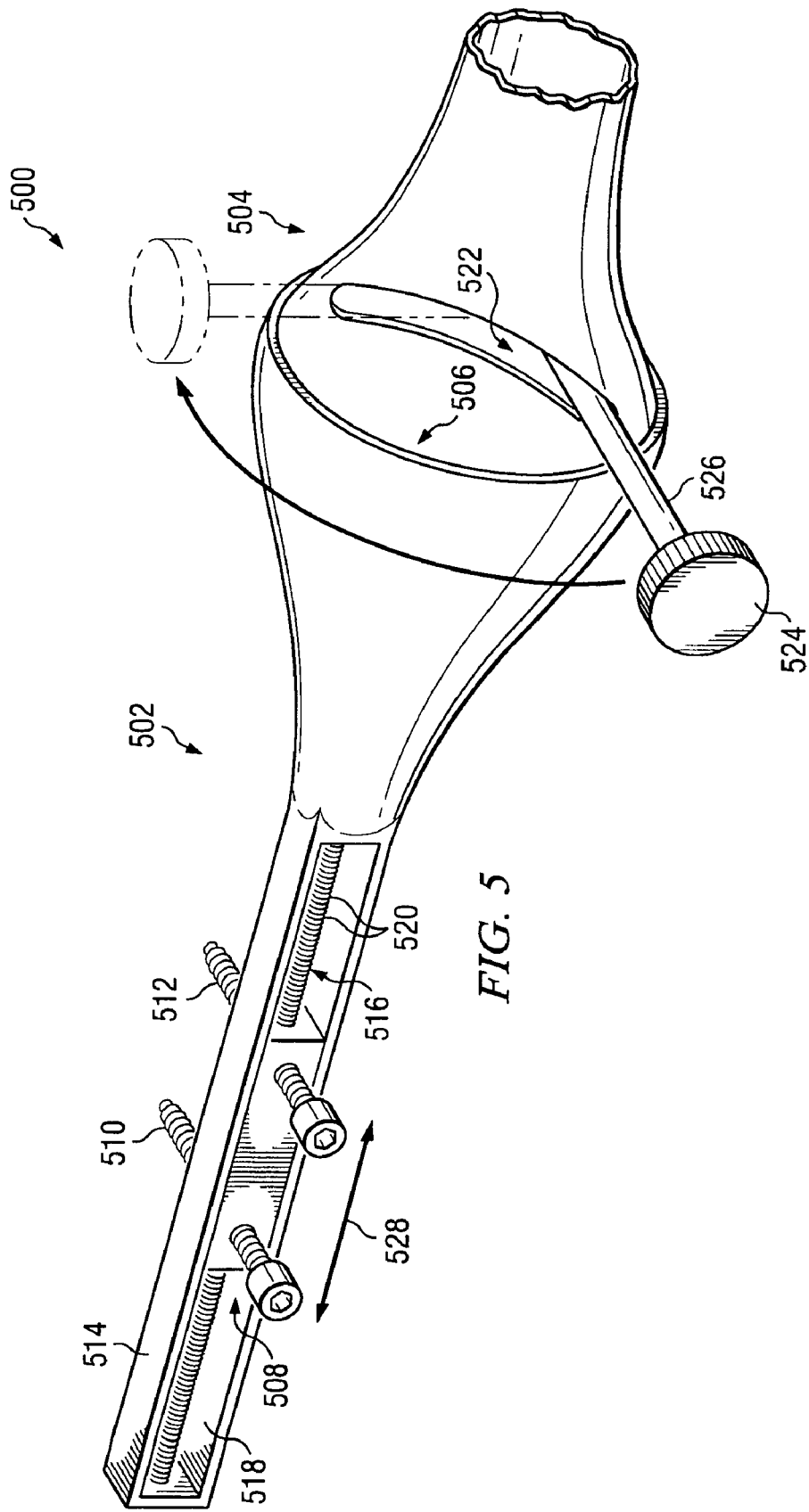
FIG. 5 shows a perspective view of an embodiment of a fixation device.

Turning next to FIG. 5, a view of an external fixation device 500 is shown that incorporates teachings of the present disclosure. For example, the device 500 can be attached to a patient's arm and hand (not shown) for treating a wrist contracture. Such an external fixation device 500 may be used to treat a wide variety of contractures in skeletal joints, either congenital or acquired. However, fixation equipment and methods incorporating teachings of the present disclosure may be used in other orthopedic applications including, but not limited to, fractures and bone lengthening. External fixation device 500 may be satisfactorily used to treat a wide variety of orthopedic indications. A fixation device incorporating teachings of the present disclosure may be formed from a wide variety of materials. For some applications external fixation device 500 may be formed from aluminum and/or stainless steel or other metal alloys satisfactory for use in treating orthopedic indications. For other applications various components and parts associated with external fixation device 500 may be formed from high strength composite materials and/or cermets.

The particular embodiment of the fixation device 500 shown in FIG. 5 is designed to accomplish two separate but related goals. First, it employs a control-drive system allowing for the type of precise and calibrated movements needed to allow medical professionals to properly orient the fixation device 500 to stretch and/or support an injured body part in the proper orientation for healing. This precise control allows for effective initial orientation of the fixation device 500, as well as simplifying any periodic re-orientation of the fixation device 500 throughout the treatment process. In addition, the disclosed embodiment improves the effectiveness of the fixation device 500 by allowing for natural bone alignment despite the rotation introduced by the fixation device 500. It may maintain a common point of origin of rotation for both the fixation device 500 and the injured body part, thus preventing any unwanted compression forces upon the bone that could delay healing.

Accordingly, the fixation device 500 disclosed below can be configured to address either or both of these goals, thereby assisting in the healing process. While the embodiment illustrated in FIG. 5 is designed to accomplish both goals simultaneously, those skilled in the art will understand that the fixation device may be configured to accomplish either of these purposes alone as well. Furthermore, persons skilled in the art will recognize that FIG. 5 discloses but one, exemplary embodiment of such a fixation device. These and all other equivalent embodiments are intended to be included within the scope of the disclosure.

In the disclosed embodiment of FIG. 5, external fixation device 500 includes a first portion 502 and a second portion 504 connected by an adjustable joint 506. For example, the adjustable joint 400 or 450 described herein can be used as the adjustable joint 506. The adjustable joint 506 can thus be used to position the first portion 502, which serves as a driven article, relative to the second portion 504 as desired. For example, the first portion 502 can be rotated or articulated as desired relative to the second portion 504, for example as shown in FIGS. 4B and 4C.

The first portion 502 includes a clamp assembly 508 for securing a pair of bone screws 510 and 512. The second portion 504 can also, in some embodiments, be provided with a clamp assembly and bone screws (not shown) substantially identical or different to those provided for the first portion depending on the application. The first portion 502 also includes a housing 514 having a generally elongated rectangular configuration. A drive screw 516 is disposed within the housing 514. In some embodiments, the second portion 504 can also be provided with a housing and drive screw (not shown) substantially the same as those provided for the first portion or substantially different depending on the application.

The housing 514 includes an elongated slot or opening 518. The drive screw 516 can be rotatably disposed within the elongated slot 518. Threads 520 are formed on the exterior of the drive screw 516 and engaged with the clamp assembly 508 whereby rotation of the drive screw 516 will result in longitudinal movement of the clamp assembly 508 relative to the adjustable joint 506 and the second portion 504.

The adjustable joint 506 rotatably connects the first and second portions 502 and 504. In the embodiment shown in FIG. 5, the adjustable joint 506 allows for controlled rotation of the first portion 502 in a generally horizontal plane relative to the second portion 504 which also corresponds generally with a plane extending through bone screws 510 and 512. The adjustable joint 506 also allows for controlled rotation of the first portion 502 in a generally vertical plane relative to the second portion 504 which also corresponds generally with movement perpendicular to the plane extending through the bone screws 510 and 512.

The adjustable joint 506 includes a drive system 522 for providing desired controlled rotation or articulation of the first portion 502 relative to the second portion 504. Any of the drive systems 100, 300, or 350, or equivalents thereof can be used as the drive system 522. The drive system 522 includes a thumb wheel 524, which serves as a control element, and a shaft 526. The thumb wheel 524 and shaft 526 can be moved between a first position (shown in solid lines) and a second position (shown in broken lines) for turning the drive system 522. In the first position, the thumb wheel 524 can be rotated for rotating the first portion 502 in the generally horizontal plane. In the second position, the thumb wheel 524 can be rotated for rotating the first portion 502 in the generally vertical plane. In this way, the use of the adjustable joint 506 in conjunction with the drive system 522 and thumb wheel 524 improves control over the positioning of the elements of the fixation device 500.

It may also be beneficial to structure the drive system 522 so that a common point of origin if rotation is maintained. Generally, this would be accomplished by providing for simultaneous longitudinal translation accompanying any rotation, in order to ensure that no compression forces are inadvertently introduced to the injured body part. By way of example, the drive system 522 can also be used to rotate a drive screw 516 (in addition to orienting the first portion 502 of the fixation device 500 with respect to the second portion 504), resulting in longitudinal translation of the clamp assembly 508 and the bone screws 510 and 512 as indicated by arrows 528. In other words, turning the thumb wheel 524 can result in simultaneous rotation of the first portion 502 and translation of the clamp assembly 508 and bone screws 510 and 512. Accordingly, the external fixation device 500 generally utilizes the motion between the first portion 502 and the second portion 504 to rotate the drive screw 516. In this regard, rotation of the drive screw 516 may be considered an indirect result of turning the thumb wheel 524.

Figure 6A:
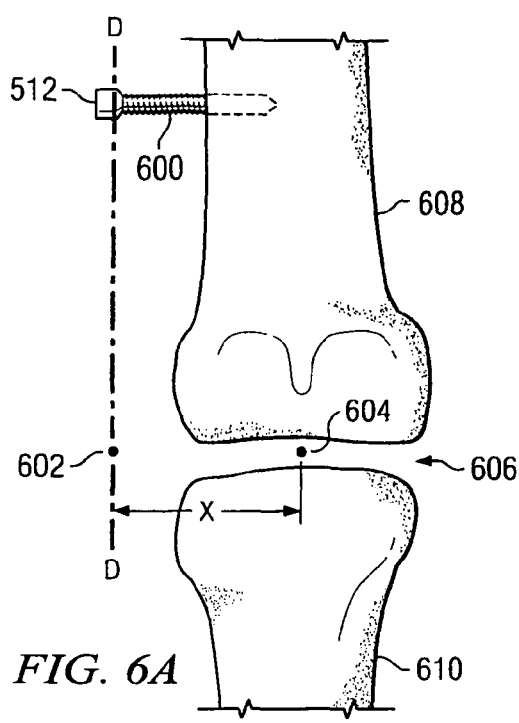
FIGS. 6A-6C show plan views for explaining the rotational and translational action of the fixation device shown in FIG. 5.

The simultaneous rotation of the first portion 502 and translation of the bone screws 510 and 512 is preferable for reasons described with reference to FIGS. 6A-6C. Referring first to FIG. 6A, an axis D-D is shown that represents a longitudinal axis of the first portion 502. A bone screw 600 is shown for fixing the first portion 502 of the fixation device 500 (not shown in FIGS. 6A-6C) to a first bone 608. A first origin of rotation point 602 represents a point about which the fixation device 500 rotates when the joint 506 is controlled for rotating the first portion 502 in the generally horizontal plane. An origin of rotation point 604 represents the natural origin of rotation for a joint 606 between the first bone 608 and a second bone 610. Note that the first and second origin points 602 and 604 are offset by a fixed distance X, which remains fixed for each of the FIGS. 6A-6C.

Figure 6B:
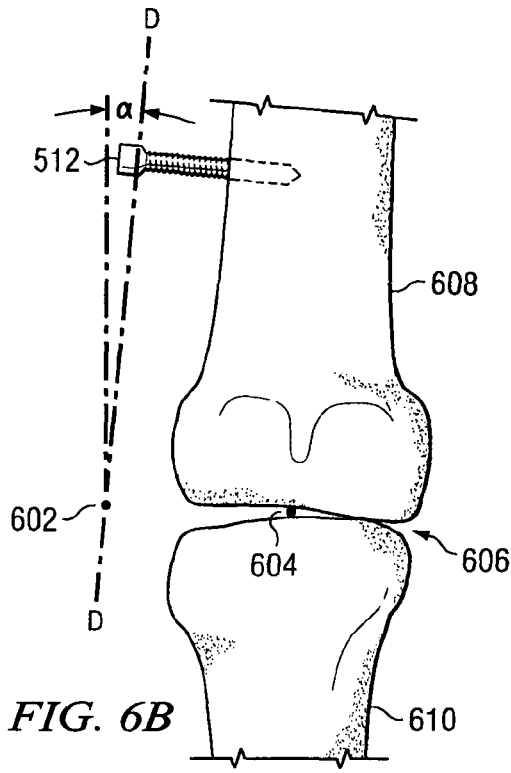

FIG. 6B shows the results of the adjustable joint 506 rotating the first portion 502 by an angle α about the first point 602 in the generally horizontal plane. In this case, the distance between the point 602 and the bone screw 512 remained fixed while the first portion 502 was rotated. As a result, rotation about the point 602 of the adjustable joint 506 causes compression of the bone gap at the joint 606.

Figure 6C:
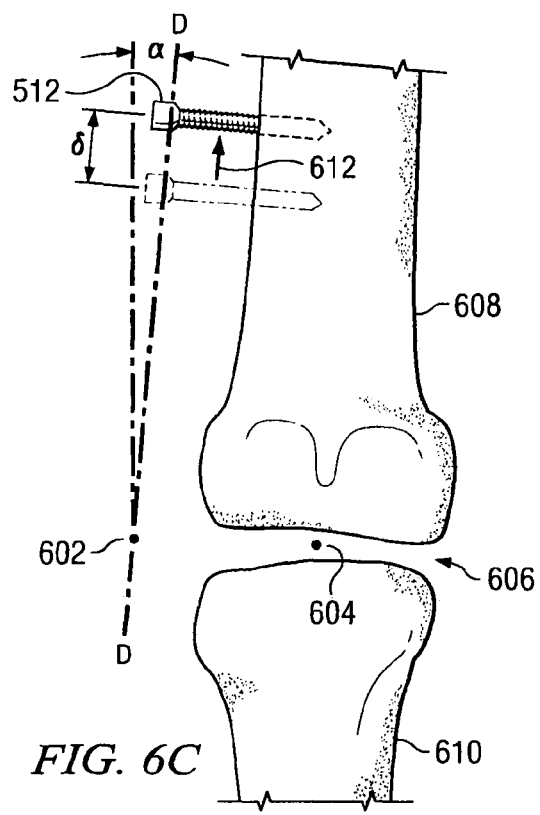

FIG. 6C, on the other hand, shows the results of rotating the first portion 502 in the same manner as it is rotated in FIG. 6B except that the bone screw is translated in the direction indicated by arrow 612 by a distance 6. In other words, while the first portion 502 was rotating by the angle δ, the bone screw 512 was translating such that the distance between the point 602 and the bone screw 512 increased by the distance 6. Translating the bone screw 512 while the first portion 502 is rotating effectively transfers the origin of rotation to point 604 so that the rotation of the bone 608 can be maintained about the natural origin of rotation for the joint 606. Preferably the amount of translation 6 of the bone screw 512 is determined based on the following relationship:

$$\delta = X \cos(\alpha) \qquad \text{Equation (1)}$$

Thus, the desired amount of translation 6 can be determined based on a function of the amount of rotation a of the adjustable joint 506 and the offset X between the first and second origin of rotation points 602 and 604.

Turning back to FIG. 5, the drive system 522 can be coupled with the drive screw 516, for example via a gear system (not shown), so that the drive screw 516 rotates as the thumb wheel 524 is rotated. This allows for longitudinal translation of the clamp assembly 508, and thus of the bone screws 510 and 512, as the first portion 502 is rotated. Preferably the drive screw 516 is set to rotate such that the clamp assembly 508 moves according to equation (1) shown above, where X is the distance between the origin of rotation of the adjustable joint 506 and the natural origin of rotation of a joint (e.g., joint 606) and α is the angle by which the first portion 502 is rotated relative to the second portion 504.

Thus, turning the thumb wheel 524 can result in simultaneous rotation of the first portion 502 and translation of the clamp assembly 508 and bone screws 510 and 512 such that a joint 606 is rotated about its natural origin of rotation 604. So in the exemplary embodiment of FIG. 5, a single fixation device 500 incorporates a fine control-drive mechanism which provides for simultaneous translation while introducing rotation (ensuring proper alignment and natural support for the injured body part). While the drive system 522 and the use of simultaneous translation in conjunction with rotation of the fixation device 500 may be used separately, it is particularly beneficial to combine both of these elements into a single device.

While various embodiments in accordance with the principles disclosed herein have been described above, it should be understood that they have been presented by way of example only, and are not limiting. For example, control elements other than a thumb wheel and drive elements other than a drive wheel are contemplated. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A device comprising:
   a control element;
   a drive element coupled to the control element; wherein the control element is operable to rotate the drive element about a first axis, and wherein the control element is further operable to angularly reposition the drive element between at least a first position and a second position about a second axis that is substantially orthogonal to the first axis;
   a housing that supports the drive element, wherein the housing is configured to prevent translational movement of the drive element; and
   a driven article coupled to the drive element such that when the drive element is in the first position, rotation of the drive element causes the driven article to move translationally in a first direction, and when the drive element is in the second position, rotation of the drive element causes the driven article to move translationally in a second direction, wherein the driven article comprises a socket member having a contact surface coupled to the drive element, and the socket member and the housing are rotatably joined.

2. A device as in claim 1, wherein the driven article and the drive element are coupled frictionally.

3. A device as in claim 1, wherein the drive element comprises a cogged wheel and wherein the driven article comprises a substrate having a plurality of recesses sized to receive cogs, wherein the engagement between the cogs of the drive wheel and the recesses of the substrate couples the driven article and the drive element.

4. A device as in claim 3 further comprising a locking mechanism, wherein the locking mechanism acts to fix the position of the driven article with respect to the housing whenever the drive element is turned between the first position and the second position.

5. A device as in claim 4, wherein the locking mechanism comprises a sheath with teeth along its bottom edge, and wherein contact between the teeth of the sheath and the recesses of the substrate serves to fix the position of the substrate with respect to the housing.

6. A device as in claim 1, wherein the control element and the drive element are rigidly coupled together, such that rotation of the control element results in rotation of the drive element.

7. A device as in claim 1, wherein the control element and the drive element are coupled together by a gear train, such that rotation of the control element results in rotation of the drive element.

8. A device as in claim 1 further comprising a locking mechanism, wherein the locking mechanism acts to fix the position of the driven article with respect to the housing whenever the drive element is turned between the first position and the second position.

9. A device as in claim 8, wherein the locking mechanism is coupled to the housing, and wherein the locking mechanism fixes the driven article in place with respect to the housing by frictionally contacting the driven article.

10. A device as in claim 1, wherein:
the housing comprises a slot;
the control element is coupled to the drive element through the slot; and
the slot allows the drive element to be turned from the first position to the second position.

11. A device as in claim 1, wherein:
the housing comprises a lower edge and the socket member comprises an upper edge, wherein the lower edge's outer diameter is larger than the upper edge's inner diameter, and wherein the lower edge of the housing fits inside the socket member below the upper edge of the socket member to rotatably join the socket member and the housing.

12. A device as in claim 1 further comprising a clamp assembly coupled to either the housing or the socket member such that rotation of the socket member with respect to the housing results in longitudinal translation of the clamp assembly.

13. A device as in claim 12 further comprising a drive screw, wherein the drive screw couples the clamp assembly to the control element such that rotation of the control element causes rotation of the socket member with respect to the housing and simultaneously causes longitudinal translation of the clamp assembly.

14. A device as in claim 13, wherein the clamp assembly further comprises one or more bone screws for attaching the clamp assembly to an injured body part.

15. A device as in claim 14, wherein the clamp assembly is removably attached to a bone at a fixed distance, and wherein the amount of longitudinal translation of the clamp assembly approximates the product of the fixed distance between the clamp assembly and the bone and the cosine of the amount of rotation of the socket member with respect to the housing.

16. A device comprising:
a first portion positioned along a first axis;
a second portion positioned along a second axis, the second axis intersecting the first axis at a rotation point;
an adjustable joint rotatably connecting the first portion and the second portion, such that the first axis may rotate with respect to the second axis at the rotation point in at least two distinct planes; and
a clamp assembly coupled to the first portion and positioned along the first axis, wherein the clamp assembly comprises one or more bone screws allowing the first portion to be releasably attached to a bone at a fixed distance; and
wherein rotation of the first portion with respect to the second portion occurs simultaneously with longitudinal translation of the clamp assembly along the first axis, wherein the amount of longitudinal translation of the clamp assembly approximates the product of the fixed distance between the first portion and the bone and the cosine of the amount of rotation of the first portion with respect to the second portion.

17. A device as in claim 16, wherein:
the adjustable joint further comprises a control element;
wherein the control element can be moved between first and second positions corresponding to the two planes of rotation of the first axis with respect to the second axis; and
wherein the control element is operable to simultaneously rotate the first portion relative to the second portion and translate the clamp assembly relative to the second portion.

18. A device as in claim 17, wherein the clamp assembly comprises one or more bone screws allowing the first portion to be releasably attached to a bone at a fixed distance; and wherein the amount of longitudinal translation of the clamp assembly approximates the product of the fixed distance between the first portion and the bone and the cosine of the amount of rotation of the first portion with respect to the second portion.

19. A device as in claim 17 further comprising a drive screw, wherein the drive screw couples the clamp assembly to the control element such that rotation of the control element causes rotation of the first portion with respect to the second portion and simultaneously causes longitudinal translation of the clamp assembly.

* * * * *